United States Patent
Sharma et al.

(10) Patent No.: US 11,193,146 B2
(45) Date of Patent: Dec. 7, 2021

(54) PROCESS FOR SECOND GENERATION ETHANOL PRODUCTION

(71) Applicants: Indian Oil Corporation Limited, Maharashtra (IN); Department of Biotechnology, New Delhi (IN)

(72) Inventors: Ajay Kumar Sharma, Haryana (IN); Manas Ranjan Swain, Haryana (IN); Ajit Singh, Haryana (IN); Anshu Shankar Mathur, Haryana (IN); Ravi Prakash Gupta, Haryana (IN); Suresh Kumar Puri, Haryana (IN); Sankara Sri Venkata Ramakumar, Haryana (IN)

(73) Assignees: Indian Oil Corporation Limited, Mumbai (IN); Department of Biotechnology, New Delhi (IN)

( * ) Notice: Subject to any disclaimer, the term of this patent is extended or adjusted under 35 U.S.C. 154(b) by 0 days.

(21) Appl. No.: 16/910,816

(22) Filed: Jun. 24, 2020

(65) Prior Publication Data

US 2020/0407759 A1  Dec. 31, 2020

(30) Foreign Application Priority Data

Jun. 26, 2019  (IN) .............................. 201921025442

(51) Int. Cl.
C12P 7/14 (2006.01)
C12P 19/14 (2006.01)

(52) U.S. Cl.
CPC ................. *C12P 7/14* (2013.01); *C12P 19/14* (2013.01); *C12P 2203/00* (2013.01)

(58) Field of Classification Search
None
See application file for complete search history.

(56) References Cited

U.S. PATENT DOCUMENTS

2012/0308991 A1* 12/2012 Eiteman .................... C12P 7/16 435/3
2014/0134692 A1* 5/2014 Ropars ...................... C12P 7/10 435/162

(Continued)

FOREIGN PATENT DOCUMENTS

WO   WO-2010/060050 A2   5/2010

OTHER PUBLICATIONS

Yadav et al., "Bioethanol fermentation of concentrated rice straw hydrolysate using co-culture of *Saccharomyces cerevisiae* and *Pichia stipitis*", Bioresource Technology, vol. 102, pp. 6473-6478, 2011 (Year: 2011).*

(Continued)

*Primary Examiner* — Richard C Ekstrom
(74) *Attorney, Agent, or Firm* — Blank Rome LLP

(57) ABSTRACT

The present invention relates to an improved method of second generation ethanol production from a lignocellulosic biomass. The process comprises subjecting a slurry of pre-treated lignocellulosic biomass comprising C5 and C6 sugars in a fermentor; preferentially fermenting mainly C5 sugars by incubating the pretreated lignocellulosic biomass of step (i) with first cellulase enzyme, co-fermenting microorganism, nutrient in the fermentor at 30-37° C. for a period of 16 to 24 hours; adding second cellulase enzyme to the fermentation broth of step (ii) and increasing the temperature to 45-55° C. for hydrolysis; allowing the fermentation broth of step (iii) to cool to a temperature of 35-38° C.; and preferentially fermenting C6 sugars by incubating the broth of step (iv) with a second dose of co-fermenting microorganism for a period of 6-8 hours to obtain ethanol. The process results in high ethanol productivity in shortest duration of time.

11 Claims, 2 Drawing Sheets

(56) References Cited

U.S. PATENT DOCUMENTS

| | | | |
|---|---|---|---|
| 2014/0170723 A1* | 6/2014 | Dobson | C12P 19/14 |
| | | | 435/165 |
| 2014/0227757 A1 | 8/2014 | Jin | |
| 2014/0273134 A1* | 9/2014 | Nghiem | C12P 7/14 |
| | | | 435/162 |
| 2015/0037856 A1* | 2/2015 | Larsen | C12P 7/14 |
| | | | 435/162 |
| 2015/0056674 A1* | 2/2015 | Harcum | C12P 7/14 |
| | | | 435/162 |
| 2015/0176034 A1* | 6/2015 | Ramos | C12P 7/10 |
| | | | 435/162 |
| 2016/0298142 A1 | 10/2016 | Yu et al. | |
| 2020/0407759 A1* | 12/2020 | Sharma | C12P 7/10 |

OTHER PUBLICATIONS

Choudhari et al., "Hydrolytic potential of cellulases from Penicillium funiculosum and Trichoderma reesei against physico-chemically different feedstocks", Advances in Biotechnology and Microbiology, 2017; 5(2): 555665. DOI: 10.19080/AIBM.2017.05.555665. (Year: 2017).*
European Search Report in EP 20182192, Nov. 17, 2020 (Year: 2020).*
Comments in European Search Report for EP 20182192, Nov. 17, 2020 (Year: 2020).*

* cited by examiner

PROCESS FOR SECOND GENERATION ETHANOL PRODUCTION

RELATED APPLICATION

This application claims the benefit of Indian Application No. 201921025442, filed on Jun. 26, 2019. The entire disclosure of this application is hereby incorporated by reference.

FIELD OF THE INVENTION

The present invention relates to a method of second generation ethanol production. More particularly, the present invention relates to a process of ethanol production from a lignocellulosic biomass. The present invention involves addition of biomass hydrolyzing enzymes from two different sources at different time intervals for better ethanol yield.

BACKGROUND OF THE INVENTION

Simultaneous saccharification fermentation/co-fermentation (SSF/SSCF) removes sugar inhibition on enzymatic hydrolysis, thus increases the hydrolysis, sugar yield and reduces the contamination risk. Moreover, SSF/SSCF reduces the overall reaction time and reactor volume (Kristensen et al., 2009). SSF/SSCF sacrifices the optimal conditions for both enzymatic hydrolysis and fermentation. Typically enzymatic hydrolysis and fermentation in SSF system, the temperature is kept at 37° C. as a compromise for better enzymatic hydrolysis and fermentation (Dien et al., 2003b). In addition, SSF/SSCF introduces a new inhibitor (ethanol) for enzymatic hydrolysis. But the inhibitory effect from ethanol is much lower compared to cellobiose or glucose (Taherzadeh & Karimi, 2007).

The major advantage of Separate Hydrolysis fermentation/co-fermentation (SHF/SHCF) compared to SSF/SSCF is that enzymatic hydrolysis and fermentation can be carried out at their own optimal conditions (Taherzadeh & Karimi, 2007). However, enzymes during hydrolysis is easily inhibited by its end-products (sugars), especially during high solids loading enzymatic hydrolysis (Kristensen et al., 2009; Philippidis & Smith, 1995), which demands somewhat longer hydrolysis time and high enzyme loading to achieve high sugar conversions. Another problem of this process is the high risk of contamination during enzymatic hydrolysis due to the long reaction time and high sugar concentrations (Taherzadeh & Karimi, 2007). Enzymatic hydrolysis is the limiting step for SHF, which determines the overall ethanol yield (Lau & Dale, 2009).

WO2010060050A2 relates to methods of converting lignocellulosic materials to alcohol that include increasing the fiber consistency of enzymatic hydrolysis mixtures. The document describes fermenting pretreated biomass that involves simultaneous saccharification (e.g., hydrolysis) and fermentation (SSF). Further, it discloses use of two different enzyme composition of cellulase enzyme i.e. first enzyme composition and second enzyme composition, in range of 5 FPU-85 FPU.

US20160298142A1 relates to a method for preparing bioethanol from lignocellulosic biomass. The document discloses simultaneous saccharification (e.g., hydrolysis) and fermentation of biomass using cellulase or cellulase enzyme complex.

US20140227757 A1 describes an integrated biological process for cellulosic bioproduct production. The integrated process can be an integrated separate hydrolysis and fermentation (SHF) process or an integrated fast simultaneous saccharification and co-fermentation (FSSCF) process. Further, the process uses AFEX (ammonium fiber explosion) pretreated biomass and utilizes three commercial enzymes in high doses.

IN2018 21008982 discloses a process wherein the free form of C5 sugars in the acid pretreated biomass was targeted first for the fermentation using C5 utilizing yeast at low temperature (30° C.) along with the cellulase enzyme. Further, the temperature of the process was increased to 50° C. for better cellulolytic hydrolysis for 24 hours and then temperature of process reduced to 35° C. for better fermentation of C6 sugar by adding a second dose of yeast to the fermentation broth.

Although, available literature provides several methods for ethanol production, however, the available methods face several challenges such as high risk of contamination during enzymatic hydrolysis due to long reaction time and high sugar concentration. Further, these methods also require longer hydrolysis time. Thus, there is a need to develop a method of ethanol production which results in higher ethanol productivity in shortest duration of time.

SUMMARY OF THE INVENTION

In an aspect of the present disclosure, there is provided a process for production of ethanol from a lignocellulosic biomass, the process comprising subjecting slurry of a pretreated lignocellulosic biomass comprising C5 and C6 sugars in a fermentor; preferentially fermenting mainly C5 sugars by incubating the pretreated lignocellulosic biomass of step (i) with first cellulase enzyme, co-fermenting microorganism, nutrient in the fermentor at 30-37° C. for a period of 16 to 24 hours; adding second cellulase enzyme to the fermentation broth of step (ii) and increasing the temperature to 45-55° C. for hydrolysis; allowing the fermentation broth of step (iii) to cool to a temperature of 35-38° C.; and preferentially fermenting C6 sugars by incubating the broth of step (iv) with a second dose of co-fermenting microorganism for a period of 6-8 hours to obtain ethanol.

In an embodiment, the present invention provides a process for production of ethanol wherein the lignocellulosic biomass is pretreated with a dilute acid.

In another embodiment, the present invention provides a process of production of ethanol wherein the process additionally comprises adjusting pH of the slurry to 5-5.5 with a pH adjuster.

In an embodiment, the present invention provides a process of production of ethanol wherein the pH adjuster is aqueous ammonium hydroxide, NaOH, KOH and CaCO3 or any other alkaline pH adjuster.

In another embodiment, the present invention provides a process wherein the pretreated biomass slurry is added in the fermentor without any detoxification.

In an embodiment, the present invention provides a process for ethanol production wherein the first cellulase enzyme is obtained from *Pencillium finiculosum* MRJ16.

In another embodiment, the present invention provides a process wherein the first cellulase enzyme is added in the concentration of 1.0-5.0 FPU/gTS.

In an embodiment, the present invention provides a process wherein the second cellulase enzyme is Ctec 3 or any other cellulase hydrolyzing enzyme which include lytic polysaccharide monooxygenases.

In another embodiment, the present invention provides a process wherein the second cellulase enzyme is added in the concentration of 0.2-1.0 FPU/gTS.

In an embodiment, the present invention provides a process of ethanol production wherein the pH adjusted slurry is fortified with a nutrient selected from MgSO4, ammonium sulphate or combination thereof.

In another embodiment, the present invention provides a process wherein the co-fermenting microorganism is selected from *Saccharomyces cerevisiae, Pichia* sp., *Candida* sp., and *E. coli* or any ethanogenic co-fermenting microorganism.

In yet another embodiment, the present invention provides a process wherein the lignocellulosic biomass is selected from the group consisting of rice straw, wheat straw, sugarcane bagasse, cotton stalk, barley stalk, bamboo or any agriculture residues which contain cellulose or hemicellulose or both.

In still another embodiment, the present invention provides a process wherein the C5 sugar is xylose and C6 sugar is glucose.

In an embodiment, the present invention provides a process which yields 2.0%-5.0% (W/V) ethanol titer within 48 hours of fermentation.

These and other features, aspects, and advantages of the present subject matter will be better understood with reference to the following description. This summary is provided to introduce a selection of concepts in a simplified form.

DETAILED DESCRIPTION OF THE INVENTION

Figure 1:
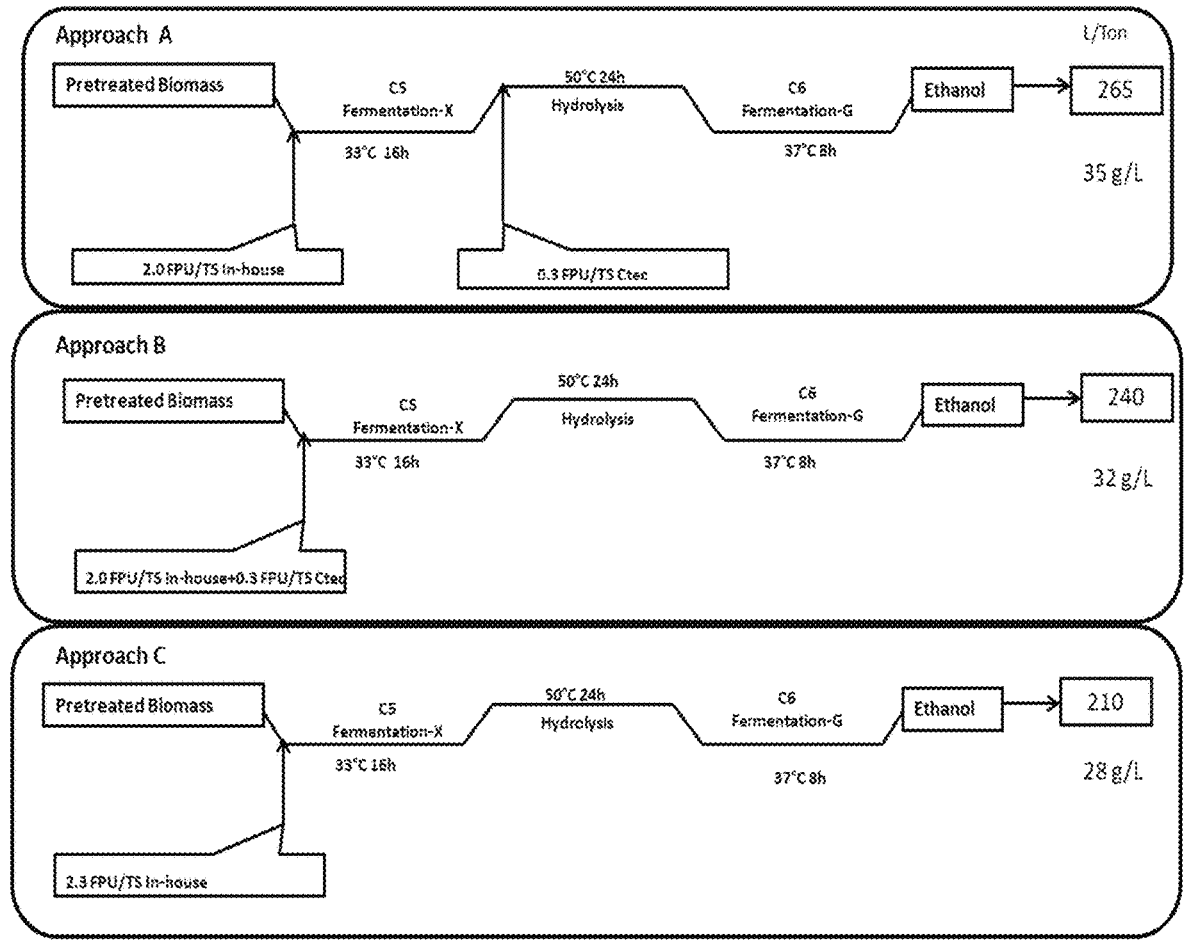
FIG. 1 illustrates schematic representation of ethanol production process in three different approaches A, B and C. Approach A: Enzyme added to the SSCF in fractional manner 2.0 FPU/gTS (obtained from *P. funiculosum* MRJ-16) at the time of fermentation (33° C.) and 0.3 FPU/gTS Ctec at the time of hydrolysis (50° C.). Approach B: Enzyme cocktail of cellulase enzyme (2.0 FPU/gTS obtained from *P. funiculosum* MRJ 16 and 0.3 FPU/gTS Ctec3) at the time of initial fermentation step (33° C.) in SSCF and Approach C: Cellulase enzyme (obtained from *P. funiculosum* MR-16) 2.3 FPU/gTS (a single source of enzyme) added to SSCF at the time of initial fermentation at (33° C.) fermentation.
Figure 2:
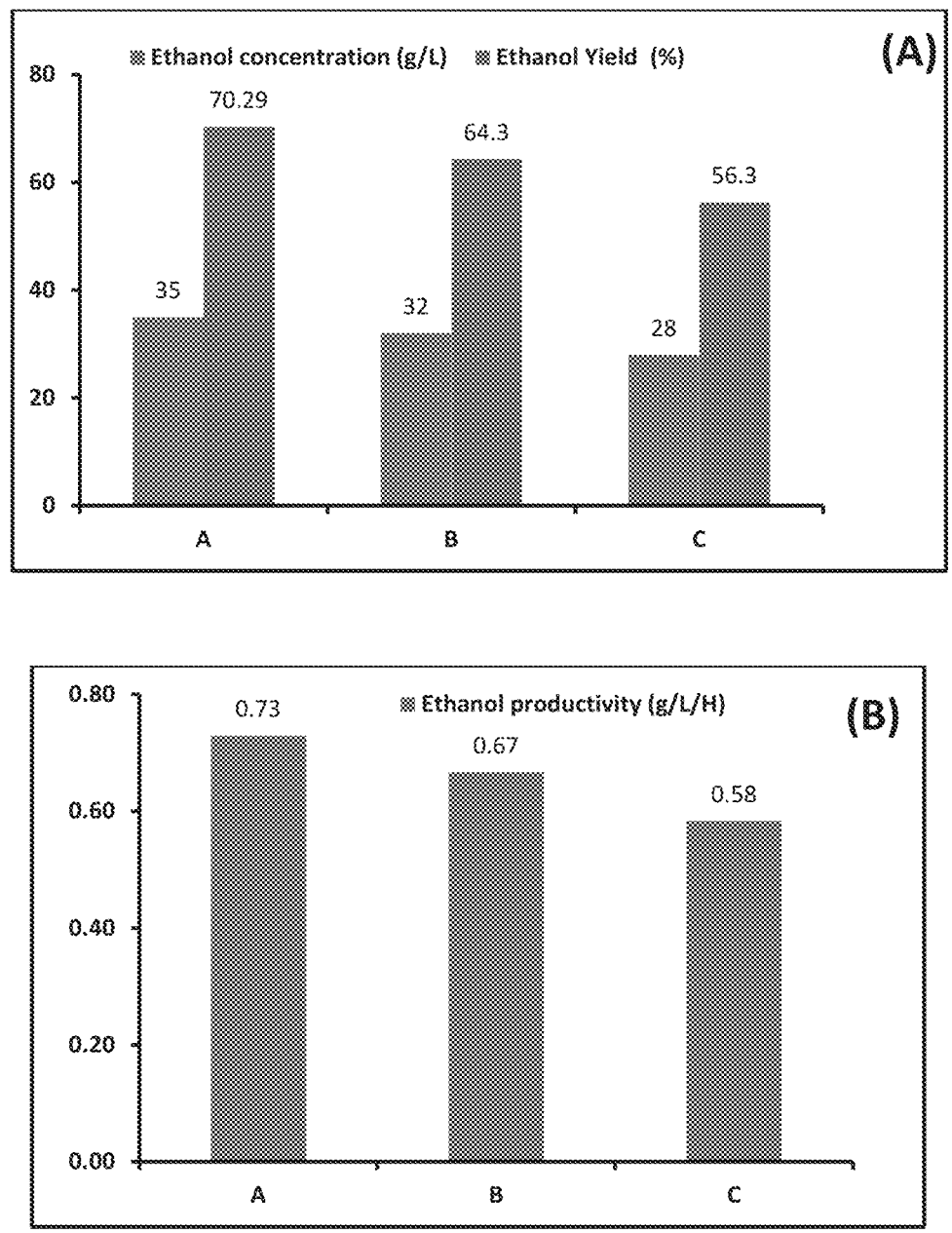
FIG. 2 illustrates ethanol concentration, yield and ethanol productivity in three different approaches A, B and C.

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

Definition

For the purposes of this invention, the following terms will have the meaning as specified therein: The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to" "including" and "including but not limited to" are used interchangeably.

Nearly all forms of lignocellulosic biomass, i.e., plant biomass, such as monocots, comprise three primary chemical fractions: hemicellulose, cellulose, and lignin. Cellulose and hemicelluloses in plant cell walls exist in complex structures within the residual material. Hemicellulose is a polymer of short, highly-branched chains of mostly five-carbon pentose sugars (xylose and arabinose), and to a lesser extent six-carbon hexose sugars (galactose, glucose and mannose). Because of its branched structure, hemicellulose is amorphous and relatively easy to hydrolyze into its individual constituent sugars by enzyme or dilute acid treatment. Cellulose is a linear polymer comprising of β(1→4) linked D-glucose in plant cell wall, much like starch with a linear/branched polymer comprising of α (1→4) linked D-glucose, which is the primary substrate of corn grain in dry grain and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers.

Therefore, a pretreatment process is typically used to alter and open up the cell wall matrix, to hydrolyze the hemicelluloses, and to reduce crystallinity. Pretreatment disrupts the non-easily digestible portion of lignocellulosic biomass, e.g., cellulose and lignin, thus improving its digestibility. After pretreatment, much of the biomass becomes easily digestible while a portion remains non-easily digestible. Ultimately, the pretreatment process makes the cellulose and/or hemicellulose more accessible (during a subsequent hydrolysis process) for conversion of the carbohydrate polymer into fermentable sugars.

"Cellulase enzyme" used herein is a mixed form of enzyme which is mostly composed of exo-hydrolase, endo-hydrolase and beta-glucosidase and other auxiliary enzymes. This enzyme was mostly produced from fungal sources. Cellulase breaks down the cellulose molecule into monosaccharide and shorter polysaccharides or oligosaccharides. In the present invention the cellulase enzyme is selected from two different sources. More particularly, the first cellulase enzyme used in the present invention is obtained from *P. funiculosum* MRJ16 and the second cellulase enzyme CTec3 is commercially obtained.

"Pretreated biomass" or "Pretreatment of biomass" used herein clears away physical and chemical barriers that make native biomass recalcitrant and exposes cellulose for better enzymatic hydrolysis. In most of the pretreatment, chemical (acid or alkali) and physical (high temperature or pressure) parameters are used individually or in mixed manner to remove barriers for enzymatic hydrolysis and improve the enzymatic digestibility.

"Detoxification" used herein is the process where the inhibitors (toxic compound such hydroxymethyl furfural, furfural, acetic acids, formic acids etc.) produced during the pretreatment process are removed or neutralized from pretreated biomass by chemical, physical or biological process.

"Total Solid (TS)" used herein contains water soluble solids and water insoluble solids in a pretreated slurry.

"Free sugar" used herein is the monomeric form of sugar which are produced from the lignocellulosic biomass during the pretreatment. Free sugar in this process composed of mainly glucose and xylose.

"C5 sugars" used herein C5 sugars represented for Xylose. "Free C5 sugar" used herein is sugar (mostly xylose) released from the hemicelluloses during the pretreatment and some part in enzymatic hydrolysis.

"C5 fermentation" used herein is Xylose fermentation into ethanol.

"C6 sugar" used herein represents glucose.

"C6 fermentation" used herein is Glucose fermentation into ethanol.

"Nutrient" used herein is $MgSO_4$. $MgSO_4$ is used in fermentation where, $Mg^{+2}$ act as an essential enzyme cofactor and act as key structural component of most biological pathways. During fermentation $Mg^{+2}$ plays a major role for proper functioning of fermenting enzymes in yeast.

Ammonium hydroxide used in this process has dual activity, it adjusts the pH of the sulphuric acid ($H_2SO_4$) in the pretreated biomass and is simultaneously converted to ammonium sulphate (ammonium ion ($NH_4+$), when combines with the free sulphate ($SO_4^{-2}$) ions released from the sulphuric acid during the pretreatment.

The present invention provides a process for production of ethanol from lignocellulosic biomass. Particularly, the process of the present invention is based on simultaneous saccharification and co-fermentation (SSCF) mechanism. The free C5 sugar in pretreated biomass is first targeted along with available low concentration of glucose for fermentation, followed by enzymatic hydrolysis and C6 sugar fermentation in a sequential manner. Particularly, the residual unhydrolyzed biomass after first fermentation process is hydrolyzed in second stage i.e., hydrolysis at 50° C. for certain time limit (24 hours). In hydrolysis process, glucose sugar is released from the cellulose portion and small part of xylose is also released from hemicellulose portion. Thus, the final ethanol concentration in second batch fermentation is higher than the first batch of fermentation. Thereafter, temperature is reduced to 35-38° C. which ferments both glucose and xylose sugar.

The process comprises pretreatment of the lignocellulosic biomass with dilute acid. The pretreatment with acid hydrolyze xylan and make biomass accessible for enzymatic hydrolysis. The pretreated biomass slurry (TS approx. 20%$^N$) without any detoxification is subjected to the fermentor. The pH of the slurry is adjusted to 5-5.5 with 25% aqueous ammonium solution. The pH adjusted slurry is then fortified with MgSO4 (0.2%), cellulose enzyme and co-fermenting Saccharomyces cerevisiae (Ig dry cell biomass/liter) for fermentation, followed by addition of water to maintain the final biomass concentration to 15%. The fermentation process is carried out at 33° C. for a period of 16-18 hours at 200 rpm. At initial stage of fermentation, 2.0 FPU/gTS of first cellulase enzyme, obtained from P. funiculosum MRJ16 is added to the fermentation process and allowed to ferment by co-fermenting yeast. Further, upon the consumption of 95% of free xylose concentration in the slurry, the second cellulase enzyme Ctec 3 (0.3 FPU/gTS) is added to the process. The temperature is then slowly increased to 50° C. at ramping of 3 to 4° C./20 minutes. After the temperature reached at the desired target, the process is allowed to maintain the temperature for 22-24 hours for better enzymatic hydrolysis. Followed by the incubation period, the fermentation broth is allowed to cool down to a temperature of 37° C. This is followed by the addition of another dose of co-fermenting S. cerevisiae (Ig dry cell biomass/liter) for second stage of fermentation. The second fermentation is stopped once the glucose is consumed almost completely i.e. in 6 to 8 hours. The process of the present invention comprises fractional addition of cellulase enzyme obtained from two different sources, which results in improved ethanol concentration in the fermentation broth.

Thus, according to one aspect of the present invention, there is provided a process for production of ethanol from a lignocellulosic biomass, the process comprising subjecting slurry of a pretreated lignocellulosic biomass comprising C5 and C6 sugars in a fermentor; preferentially fermenting mainly C5 sugars by incubating the pretreated lignocellulosic biomass of step (i) with first cellulase enzyme, co-fermenting microorganism, nutrient in the fermentor at 30-37° C. for a period of 16 to 24 hours; adding second cellulase enzyme to the fermentation broth of step (ii) and increasing the temperature to 45-55° C. for hydrolysis; allowing the fermentation broth of step (iii) to cool to a temperature of 35-38° C.; and preferentially fermenting C6 sugars by incubating the broth of step (iv) with a second dose of co-fermenting microorganism for a period of 6-8 hours to obtain ethanol.

In an embodiment, the present invention provides a process for production of ethanol wherein the lignocellulosic biomass is pretreated with a dilute acid.

In another embodiment, the present invention provides a process of production of ethanol wherein the process additionally comprises adjusting pH of the slurry to 5-5.5 with a pH adjuster.

In an embodiment, the present invention provides a process of production of ethanol wherein the pH adjuster is aqueous ammonium hydroxide, NaOH, KOH and CaCO3 or any other alkaline pH adjuster.

In another embodiment, the present invention provides a process of production of ethanol wherein the pH adjuster other than aqueous ammonium hydroxide requires addition of ammonium sulfate in a concentration of 4 g/l.

In another embodiment, the present invention provides a process wherein the pretreated biomass slurry is added in the fermentor without any detoxification.

The process of the present invention involves fractional addition of cellulase enzymes from two different sources. The first cellulase enzyme is obtained from Penicillium funiculosum MRJ16 (MTCC Accession No. 25142 and Date of Deposition 12 Jun. 2017). P. funiculosum MRJ16 is in-house mutant of P. funiculosum NCIM 2218 which produces enzyme for hydrolyzing biomass. The second cellulase enzyme Ctec 3 is commercially obtained.

In an embodiment, the present invention provides a process for ethanol production wherein the first cellulase enzyme is obtained from Pencillium funiculosum MRJ16.

In another embodiment, the present invention provides a process wherein the first cellulase enzyme is added in the concentration of 1.0-5.0 FPU/gTS.

In an embodiment, the present invention provides a process wherein the second cellulase enzyme is Ctec 3 or any other cellulase hydrolyzing enzyme which include lytic polysaccharide monooxygenases (LPMOs).

In another embodiment, the present invention provides a process wherein the second cellulase enzyme is any enzyme which converts glucose to gluconic acid at temperature ranging from 30-37° C.

In another embodiment, the present invention provides a process wherein the second cellulase enzyme is added in the concentration of 0.2-1.0 FPU/gTS.

In an embodiment, the present invention provides a process of ethanol production wherein the pH adjusted slurry is fortified with a nutrient selected from MgSO4, ammonium sulphate or combination thereof.

In another embodiment, the present invention provides a process wherein the co-fermenting microorganism is selected from *Saccharomyces cerevisiae, Pichia* sp., *Candida* sp., and *E. coli* or any ethanogenic co-fermenting microorganism.

In yet another embodiment, the present invention provides a process wherein the lignocellulosic biomass is selected from the group consisting of rice straw, wheat straw, sugarcane bagasse, cotton stalk, barley stalk, bamboo or any agriculture residues which contain cellulose or hemicellulose or both.

In still another embodiment, the present invention provides a process wherein the C5 sugar is xylose and C6 sugar is glucose.

The process of the present invention is advantageous as the pretreated biomass slurry is subjected to the fermentor without any detoxification. Further, in this process the C5 and C6 sugars are targeted for fermentation in sequential manner to achieve higher ethanol titer in a shortest period of time of fermentation i.e. 48 hours. Moreover, the process utilizes minimum amount of enzyme in the fermentation process, which partially hydrolyzes the glucan content in the biomass. In addition, the initial xylose rich and small amount of glucose in the pretreated (with dilute acid) biomass is targeted for fermentation at initial stage which reduces the enzymatic feedback inhibition. Therefore, the process overall improves the ethanol yield and productivity in shortest time interval.

In an embodiment, the present invention provides a process which yields 2.0%-5.0% (WN) ethanol titer within 48 hours of fermentation.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1: Process for Ethanol Production

The lignocellulosic biomass (rice straw) was initially pretreated with dilute sulphuric acid. The pretreated biomass slurry (Total Solid approx. 20%) was then subjected to fermentor without any detoxification. The lignocellulosic biomass was obtained locally from District Palwal, Haryana, India. This was followed by adjusting of the pH of the slurry to 5-5.5 with 25% aqueous ammonium solution. The pH adjusted slurry was fortified with MgSO4 (0.2%), cellulase enzyme and co-fermenting *Saccharomyces cerevisiae* (1 g dry cell biomass/liter), and required amount of water was added to the process to maintain the final biomass concentration to 15%. *Saccharomyces cerevisiae* is a genetically engineered strain obtained from Belgium, which ferments both glucose and xylose. The fermentation broth was further, incubated at 33° C. for 18 hours for fermentation at 200 rpm. At initial stage of fermentation 2.0 FPU/gTS, the first cellulase enzyme (obtained from *P. funiculosum* MRJ16) was added to the fermentation process and allowed to ferment by co-fermenting yeast. Further, upon the consumption of 95% of the free xylose concentration in the slurry, the second cellulase enzyme i.e. Ctec 3 (Commercial enzyme, Novazyme) was added (0.3 FPU/g TS). This was followed by increase in the temperature of the process to 50° C. at ramping of 3 to 4° C./20 minutes. After the temperature was reached at desired target, the process was allowed to maintain the temperature for 24 hours for better enzymatic hydrolysis. The process was then, allowed to cool down to temperature 37° C. Subsequently, another dose of co-fermenting *S. cerevisiae* (Ig dry cell biomass/liter) was inoculated for the second stage of fermentation. The second fermentation was stopped once the glucose was consumed completely in 8 hours incubation period. The whole process utilized 48 hours including fermentation and enzymatic hydrolysis.

TABLE 1

| Parameters used for the SSCF process | |
|---|---|
| Solid Loading | 15% |
| Yeast biomass | 1.0 g dry cell biomass/Litre |
| Enzyme source | Ctec3, Novazyme |
| FPU/G of TS | 2.3 FPU/G of TS |
| pH adjusted by | NH$_4$OH |
| Other Nutrient | Mg SO$_4$ @ 0.2% |

Example 2: Measuring Ethanol Productivity in Three Different Approaches

Three different experiments were performed and ethanol production was measured. Particularly, in the three approaches, the cellulase enzymes from two different sources were added at different time intervals. In approach A, the cellulase enzymes was added to the process in a fractional manner as follows i.e. 2.0 FPU/gTS (enzyme obtained from *P. funiculosum* MI-16) at the time of fermentation (33° C.) and 0.3 FPU/gTS Ctec at the time of hydrolysis (50° C.).

In approach B, enzyme cocktail of cellulase enzyme 2.0 FPU/gTS (enzyme obtained from *P. funiculosum* MTJ-16)+ 0.3 FPU/gTS Ctec was added at the time of fermentation (33° C.). In approach C, 2.3 FPU/gTS (a single source of enzyme) i.e. the cellulase enzyme obtained from *P. funiculosum*) was added at the time of fermentation (33° C.).

Subsequent to the addition of the enzymes, the fermentation broth was incubated at 33° C. for 16 hours. In this incubation period, the pentose sugar was fermented to ethanol in presence of co-fermenting *S. cerevisiae*. Further, when the free xylose concentration (19.5 g/L) in the slurry was near to 2 g/l, the temperature of the process was increased to 50° C. and was allowed to maintain it for a period of 24 hours. The increase in the temperature was mainly required for better enzymatic hydrolysis of cellulose. Subsequently, the system was allowed to cool down to a temperature of 37° C. This was followed by addition of a second dose of co-fermenting *S. cerevisiae* (1 g dry cell biomass/liter) for second stage of fermentation. The second fermentation was stopped after 8 hours of fermentation. The whole process was completed in duration of 48 hours including fermentation and enzymatic hydrolysis.

TABLE 2

Ethanol concentration, yield and Ethanol productivity in the three different approaches.

| Approach | A | B | C |
|---|---|---|---|
| Ethanol concentration (g/L) | 35.00 | 32.00 | 28.00 |
| Ethanol Yield (%) | 70.29 | 64.30 | 56.30 |
| Ethanol productivity (g/L/H) | 00.73 | 00.67 | 00.58 |

Approach A: Enzyme added to the SSCF in fractional manner as follows 2.0 FPU/gTS (obtained from *P. funiculosum* MRJ-16) at the time of fermentation (33° C.)) and 0.3 FPU/gTS Ctec at the time of hydrolysis (50° C.). Approach B: Enzyme cocktail of cellulase enzyme (2.0 FPU/gTS obtained from *P. funiculosum* MRJ-16+ 0.3 FPU/gTS Ctec) at the time of fermentation (33° C.) in SSCF and Approach C: Cellulase enzyme (obtained from *P. funiculosum* MRJ-16) 2.3 FPU/gTS (a single source of enzyme) added to SSCF at the time of fermentation (33° C.).

Accordingly, the ethanol production was measured in three approaches and the results indicated that among the three approaches, the approach (A) resulted in higher ethanol concentration, yield and productivity. Thus, the results demonstrates that the process of the present invention involving fractional addition of biomass hydrolyzing enzymes (cellulase) from two different sources at different time intervals results in better ethanol yield.

We claim:

1. A two stage process for production of ethanol from a lignocellulosic biomass, the process comprising:
   i. introducing a slurry of pre-treated lignocellulosic biomass comprising C5 and C6 sugars in a fermentor;
   ii. preferentially fermenting mainly C5 sugars by incubating the pretreated lignocellulosic biomass of step (i) with a first cellulase enzyme, a first dose of co-fermenting microorganism, and a nutrient in the fermentor at 30-37° C. for a period of 16 to 24 hours;
   iii. adding a second cellulase enzyme to the fermentation broth of step (ii) and increasing the temperature to 45-55° C. for hydrolysis;
   iv. allowing the fermentation broth of step (iii) to cool to a temperature of 35-38° C.; and
   v. preferentially fermenting C6 sugars by incubating the broth of step (iv) with a second dose of co-fermenting microorganism for a period of 6-8 hours to obtain ethanol;
   wherein the first cellulase enzyme is obtained from *Pencillium funiculosum* MRJ16;
   wherein the second cellulase enzyme is Ctec 3:
   wherein the co-fermenting microorganism is *Saccharomyces cerevisiae*.

2. The process as claimed in claim 1, wherein the pre-treatment of lignocellulosic biomass in step (i) comprises treating the biomass with a dilute acid.

3. The process as claimed in claim 2, wherein the pre-treatment of biomass slurry additionally comprises adjusting pH of the slurry to 5-5.5 with a pH adjuster.

4. The process as claimed in claim 3, wherein the pH adjuster is aqueous ammonium hydroxide, NaOH, KOH, or $CaCO_3$ or any other alkaline pH adjuster.

5. The process as claimed in claim 1, wherein the pre-treated biomass slurry is added in the fermentor without any detoxification.

6. The process as claimed in claim 1, wherein the first cellulase enzyme is added in a concentration of 1.0-5.0 FPU/g TS.

7. The process as claimed in claim 1, wherein the second cellulase enzyme is added in a concentration of 0.2-1.0 FPU/g TS.

8. The process as claimed in claim 3, wherein the pH adjusted slurry is fortified with a nutrient selected from $MgSO_4$, ammonium sulphate or combination thereof.

9. The process as claimed in claim 1, wherein the lignocellulosic biomass is selected from the group consisting of rice straw, wheat straw, sugarcane bagasse, cotton stalk, barley stalk, bamboo and any agriculture residues which contain cellulose or hemicellulose or both.

10. The process as claimed in claim 1, wherein the C5 sugar is xylose and the C6 sugar is glucose.

11. The process as claimed in claim 1, wherein the process yields 2.0%-5.0% (W/V) ethanol titer within 48 hours of fermentation.

* * * * *